(12) United States Patent
Yamamoto et al.

(10) Patent No.: US 8,871,249 B2
(45) Date of Patent: Oct. 28, 2014

(54) MEDICATED PATCH

(75) Inventors: Naoki Yamamoto, Tsukuba (JP); Kumi Morimoto, Tsukuba (JP); Akio Takeuchi, Tsukuba (JP); Kenji Ishigaki, Tsukuba (JP)

(73) Assignee: Hisamitso Pharmaceutical Co., Inc., Tosu-shi, Saga (JP)

(*) Notice: Subject to any disclaimer, the term of this patent is extended or adjusted under 35 U.S.C. 154(b) by 0 days.

(21) Appl. No.: 12/919,715

(22) PCT Filed: Feb. 9, 2009

(86) PCT No.: PCT/JP2009/052177
§ 371 (c)(1),
(2), (4) Date: Sep. 13, 2010

(87) PCT Pub. No.: WO2009/107477
PCT Pub. Date: Sep. 3, 2009

(65) Prior Publication Data
US 2011/0002976 A1  Jan. 6, 2011

(30) Foreign Application Priority Data

Feb. 27, 2008 (JP) ................. 2008-046804

(51) Int. Cl.
*A61F 13/00* (2006.01)
*A61K 31/4985* (2006.01)
*A61K 9/70* (2006.01)

(52) U.S. Cl.
CPC ........... *A61K 31/4985* (2013.01); *A61K 9/7061* (2013.01)
USPC ........................................................ 424/448

(58) Field of Classification Search
None
See application file for complete search history.

(56) References Cited

U.S. PATENT DOCUMENTS 5,059,189 A * 10/1991 Cilento et al. ................. 604/307
5,676,968 A    10/1997 Lipp et al.
(Continued)

FOREIGN PATENT DOCUMENTS

EP    0 387 751 A2    9/1990
EP    0 887 075 A2    12/1998
(Continued)

OTHER PUBLICATIONS

International Preliminary Examination Report for corresponding PCT Application No. PCT/JP2009/052180; 9 pages; includes the PCT/IB/338, the PCT/IB/373, and the PCT/ISA/237; mailed on Oct. 14, 2010.

(Continued)

*Primary Examiner* — Anand Desai
*Assistant Examiner* — Melissa Mercier
(74) *Attorney, Agent, or Firm* — Nath, Goldberg & Meyer; Joshua B. Goldberg; Scott H. Blackman

(57) ABSTRACT

Provided is a medicated patch containing a medicinal agent, an adhesive base material and a tackifier, where the medicinal agent is varenicline or a pharmaceutically acceptable salt thereof, the adhesive base material is a rubbery adhesive base material and the tackifier is a rosin-based tackifier selected from the group consisting of rosin, rosin derivatives and hydrogenated products of the foregoing, or a non-rosin-based tackifier selected from the group consisting of aliphatic hydrocarbon resins and alicyclic hydrocarbon resins, and when a non-rosin-based tackifier is added as the tackifier, a solubilizer for the medicinal agent is further added, the solubilizer containing an alcohol-based solubilizer having at least a solubility parameter of 20-35.

6 Claims, 2 Drawing Sheets

(56) References Cited

U.S. PATENT DOCUMENTS

| | | |
|---|---|---|
| 5,807,570 A | 9/1998 | Chen et al. |
| 5,830,497 A | 11/1998 | Yamanaka et al. |
| 5,866,157 A | 2/1999 | Higo et al. |
| 6,146,656 A | 11/2000 | Hori et al. |
| 6,207,183 B1 | 3/2001 | Horstmann et al. |
| 6,620,429 B1 | 9/2003 | Müller |
| 6,638,528 B1 | 10/2003 | Kanios |
| 6,884,434 B1 | 4/2005 | Muller et al. |
| 6,899,894 B1 | 5/2005 | Klein et al. |
| 7,150,881 B2 | 12/2006 | Govil et al. |
| 7,175,853 B1 | 2/2007 | Bracht |
| 7,921,999 B1 | 4/2011 | Kimball |
| 2002/0192243 A1 | 12/2002 | Hsu et al. |
| 2003/0104041 A1 | 6/2003 | Hsu et al. |
| 2003/0180347 A1 | 9/2003 | Young et al. |
| 2004/0028724 A1 | 2/2004 | Terahara et al. |
| 2004/0096491 A1 | 5/2004 | Tateishi et al. |
| 2004/0220262 A1 | 11/2004 | Hsu et al. |
| 2005/0074487 A1 | 4/2005 | Hsu et al. |
| 2006/0292210 A1 | 12/2006 | Inosaka et al. |
| 2007/0098772 A1 | 5/2007 | Westcott et al. |
| 2009/0220580 A1 | 9/2009 | Kawahara et al. |
| 2010/0062046 A1 * | 3/2010 | Allen et al. ............ 424/449 |
| 2011/0086086 A1 | 4/2011 | Johnson et al. |

FOREIGN PATENT DOCUMENTS

| | | |
|---|---|---|
| EP | 1366762 | 12/2003 |
| EP | 1542177 | 6/2005 |
| EP | 1 743 645 A1 | 1/2007 |
| JP | H7506083 | 7/1995 |
| JP | H1135452 | 2/1999 |
| JP | H1147233 | 2/1999 |
| JP | H1160475 | 3/1999 |
| JP | 11-506462 A | 6/1999 |
| JP | H11209270 A | 8/1999 |
| JP | H11209271 A | 8/1999 |
| JP | 2001-518058 A | 10/2001 |
| JP | 2002-509874 A | 4/2002 |
| JP | 2002-509878 A | 4/2002 |
| JP | 2002-509879 A | 4/2002 |
| JP | 2003528045 A | 9/2003 |
| JP | 2004-83523 A | 3/2004 |
| JP | 2005-528413 A | 9/2005 |
| JP | 2005-535686 A | 11/2005 |
| JP | 2007-016020 A | 1/2007 |
| JP | 2007-16020 A | 1/2007 |
| JP | 2007016019 A | 1/2007 |
| JP | 2007031436 | 2/2007 |
| JP | 2007-176880 A | 7/2007 |
| WO | 96/16642 A1 | 6/1996 |
| WO | 96/39136 A1 | 12/1996 |
| WO | 97/11696 | 4/1997 |
| WO | 01/43734 A2 | 6/2001 |
| WO | 02/38139 A1 | 5/2002 |
| WO | 02/45701 A2 | 6/2002 |
| WO | WO 0245701 A2 * | 6/2002 |
| WO | 02/069942 A1 | 9/2002 |
| WO | 2006/040680 A1 | 4/2006 |
| WO | 2006/082728 A1 | 8/2006 |
| WO | 2006/114868 A1 | 11/2006 |
| WO | 2007/012963 A1 | 2/2007 |
| WO | 2007/094385 A1 | 8/2007 |
| WO | 2007/129712 A1 | 11/2007 |
| WO | 2008/032678 A1 | 3/2008 |

OTHER PUBLICATIONS

International Preliminary Examination Report for a related PCT Application No. PCT/JP2009/052181; 8 pages; includes the PCT/IB/338, the PCT/IB/373, and the PCT/ISA/237; mailed on Oct. 14, 2010.
International Preliminary Examination Report for a related PCT Application No. PCT/JP2009/052177; 5 pages; includes the PCT/IB/338, the PCT/IB/373, and the PCT/ISA/237; mailed on Oct. 14, 2010.
International Preliminary Examination Report for a related PCT Application No. PCT/JP2009/052175; 6 pages; includes the PCT/IB/338, the PCT/IB/373, and the PCT/ISA/237; mailed on Oct. 14, 2010.
Extended European Search Report issued Mar. 31, 2011, in the European Patent Application No. 09715476.9, seven (7) pages.
Extended European Search Report issued on Apr. 6, 2011, in counterpart European Patent Application No. 09715573.3, five (5) pages.
Extended European Search Report issued on Mar. 31, 2011, in counterpart European Patent Application No. 09715635.0.
Office Action issued for Japanese Patent Application No. P2010-500638 on Aug. 13, 2013.
Search Report for EP 09715019.7; 8 pages; mailed on Jun. 12, 2013.
"Anonymous: Transdermal and topical drug delivery", Pharmaceutical Press, 2003, p110-p111, XP002697381.
USPTO Office Action, issued on Mar. 1, 2013, in U.S. Appl. No. 12/919,723, twenty one (21) pages.
Office Action issued by the U.S. Patent and Trademark Office on Sep. 12, 2012 for U.S. Appl. No. 12/919,739; 14 pages.
Office Action issued for Japanese Patent Application No. P2010-500639 on Aug. 20, 2013.
Office Action issued by the U.S. Patent and Trademark Office on Jul. 18, 2012 for U.S. Appl. No. 12/919,723; 8 pages.
Office Action issued by the U.S. Patent and Trademark Office on Sep. 21, 2012 for U.S. Appl. No. 12/919,723; 35 pages.
Office Action issued in Japanese Patent Application No. P2010-500640 dated Sep. 24, 2013, 3 pages.
Japanese Patent Application No. P2010-500640, Notification of Information Provision dated May 13, 2014, six (6) pages.
Japanese Patent Application No. P2010-500640, Office Action dated Jul. 15, 2014, three (3) Pages.

* cited by examiner

MEDICATED PATCH

CROSS-REFERENCE TO RELATED APPLICATION

This is a National Phase Application filed under 35 U.S.C. 371 as a national stage of PCT/JP2009/052177, filed Feb. 9, 2009, an application claiming foreign priority benefits under 35 USC 119 of Japanese Application No. 2008-046804, filed on Feb. 27, 2008, the content of each of which is hereby incorporated by reference in its entirety.

TECHNICAL FIELD

The present invention relates to a medicated patch.

BACKGROUND ART

Various types of medicated patches containing medicinal agents are being developed with expectations of reducing side-effects caused by tissue absorption of the medicinal agents into the gastrointestinal tract and avoiding first pass into the liver, and of improving patient compliance.

However, not all medicinal agents exhibit satisfactory tissue absorption with transdermal administration, transmucosal administration or transnail administration, and much investigation has been conducted to improve tissue absorption.

Medicinal agents are available on the market in the form of acid addition salts, from the viewpoint of handleability and stability. However, it is generally known that when medicinal agents of acid addition salts are directly applied by transdermal administration, their tissue absorption tends to be lower. On the other hand, it is also known that free bases (free forms) of medicinal agents are preferred for tissue absorption.

Methods of neutralizing (desalting) acid addition salts of medicinal agents to be used in medicated patches, using metal hydroxides such as sodium hydroxide, as strong bases which completely desalt the acid addition salts, have been investigated (Patent documents 1 and 2, for example), but all of these methods either eliminate beforehand the metal salts produced by filtration treatment, or mix them with adhesive base materials.

[Patent document 1] Japanese Unexamined Patent Application Publication No. 2007-16020
[Patent document 2] Japanese Unexamined Patent Application Publication (Translation of PCT Application) No. 2002-509874

DISCLOSURE OF THE INVENTION

Problems to be Solved by the Invention

The present inventors have found, however, that when a medicinal agent free form and metal salt (sodium chloride or the like) are formed by neutralization reaction of the acid addition salt of the medicinal agent, and the metal salt is neutralized together with an adhesive base material without removal by filtration treatment, for application of a more convenient production method, the production stability and production properties of the medicated patch tend to be reduced.

In particular, the present inventors have found that when the convenient production method described above is applied for production of a medicated patch containing varenicline or a pharmaceutically acceptable salt thereof as the medicinal agent, the medicinal agent undergoes crystal deposition in the patch resulting in undesirable effects on the pharmaceutical properties or production stability, and that when an additive such as a solubilizer is added to inhibit such crystal deposition, the tissue permeability (cutaneous permeability) of the drug is sometimes reduced.

It is therefore an object of the present invention to provide a medicated patch comprising varenicline or a pharmaceutically acceptable salt thereof as the medicinal agent, and having both excellent medicinal agent solubility and tissue permeability.

Means for Solving the Problems

As a result of much diligent research directed toward achieving the object stated above, the present inventors have found that, even when varenicline or a pharmaceutically acceptable salt thereof is contained as the medicinal agent, adding a specific adhesive base material and tackifier can yield a medicated patch having high medicinal agent solubility that can prevent crystal deposition of the medicinal agent, and having excellent tissue permeability (cutaneous permeability).

Specifically, the invention provides a medicated patch comprising a medicinal agent, an adhesive base material and a tackifire, wherein the medicinal agent is varenicline or a pharmaceutically acceptable salt thereof, the adhesive base material is a rubbery adhesive base material and the tackifier is a rosin-based tackifier selected from the group consisting of rosins, rosin derivatives and hydrogenated products of the foregoing, or a non-rosin-based tackifier selected from the group consisting of aliphatic hydrocarbon resins and alicyclic hydrocarbon resins, and when a non-rosin-based tackifier is added as the tackifire, a solubilizer for the medicinal agent is further added, the solubilizer comprising at least an alcohol-based solubilizer having a solubility parameter of 20-35.

The medicated patch of the invention may further contain a metal salt. The metal salt contains a substance, or its constituent component, that can bond with the medicinal agent to form a medicinal agent salt, and the metal salt content is no greater than the number of moles of the substance or its constituent component that bonds with the medicinal agent to form the medicinal agent salt, when a medicinal agent salt has been formed with the same number of moles as the medicinal agent in the medicated patch.

An example of the metal salt in the medicated patch of the invention will now be explained. If the medicinal agent is represented as "A", the substance that can bond with the medicinal agent "A" to form the medicinal agent acid addition salt is represented as "HX" and the medicinal agent acid addition salt is represented as "A.HX", then the neutralization reaction can be represented by A.HX+MOH→A+MX+$H_2O$, where the salt produced by the neutralization reaction is "MX". The metal salt in the medicated patch of the invention is "MX" in this example, and it contains the constituent component "X" of the substance that can bond with the medicinal agent "A" to form the medicinal agent salt "HX". The content of "MX" is no greater than the number of moles of "HX" in "A.HX".

The tackifier in the medicated patch of the invention imparts adhesiveness to the medicated patch, and due to the presence of the tackifire, the medicated patch becomes a material with an adhesive property. The phrase "material with an adhesive property" means that it is a material that "exhibits a 1 second creep compliance larger than $1 \times 10^{-6}$ $cm^2/dyne$" at the applied temperature (for example, 30° C.-40° C.) (see Handbook of Pressure-Sensitive Adhesive Technology, Edited by D. Satas, pg. 172, (1989)).

The rosin-based tackifier not only has a function as a tackifire, but also as a solubilizer to improve the solubility of the medicinal agent in the medicated patch. It is thus possible to realize satisfactory medicinal agent solubility without impairment of excellent tissue permeability. Both excellent tissue permeability and medicinal agent solubility can also be obtained by using a combination of the aforementioned non-rosin-based tackifier and an alcohol-based solubilizer having a solubility parameter of 20-35.

Since the types of adhesive base material and tackifier are limited according to the invention as explained above, it is possible to inhibit crystal deposition during preparation of the medicinal agent, to obtain higher pharmaceutical properties. The medicated patch of the invention having this construction also has excellent tissue permeability.

The alcohol-based solubilizer is preferably a monohydric or polyhydric alcohol with a solubility parameter of 20-35, and more preferably a polyhydric alcohol with a solubility parameter of 20-35. By using a non-rosin-based tackifier and such an alcohol-based solubilizer in combination, the tissue permeability and medicinal agent solubility are further improved.

When the medicinal agent in the medicated patch of the invention is a medicinal agent in free base form produced by neutralization reaction between the medicinal agent acid addition salt and metal hydroxide, the medicated patch may contain the metal salt mentioned above. The metal salt may be produced during production as described above, or it may be produced in the medicated patch after production (that is, during the storage after production and before use).

The metal salt is preferably at least one selected from the group consisting of metal chlorides, metal bromides, metal iodides, organic acid metal salts. Particularly preferred metal salts are one or more selected from the group consisting of sodium chloride, calcium chloride, aluminum chloride, stannous chloride, ferric chloride, magnesium chloride, potassium chloride, sodium citrate, sodium oxalate, sodium tartrate, sodium bromide and sodium succinate.

The medicinal agent acid addition salt is preferably a hydrochloride, acetic acid salt, sulfuric acid salt, maleic acid salt, oxalic acid salt, citric acid salt, hydroiodic acid salt, mesylic acid salt, tartaric acid salt or succinic acid salt of a basic medicinal agent (varenicline or a pharmaceutically acceptable salt thereof).

The medicated patch of the invention may be applied directly onto the skin as a "salve", or a pressure-sensitive adhesive layer may be formed on a support and the medicated patch included in the pressure-sensitive adhesive layer for application as a plaster or the like.

Effect of the Invention

According to the invention there is provided a medicated patch comprising varenicline or a pharmaceutically acceptable salt thereof as the medicinal agent, and having both excellent medicinal agent solubility and tissue permeability.

EXPLANATION OF SYMBOLS

1: Medicated patch, 2: support, 3: pressure-sensitive adhesive layer, 4: release sheet.

BEST MODES FOR CARRYING OUT THE INVENTION

Preferred embodiments will now be explained in detail, with reference to the accompanying drawings. Also, some of the drawings are exaggerated in size for easier illustration, and the dimensional proportions will not necessarily match those in the explanation.

Figure 1:
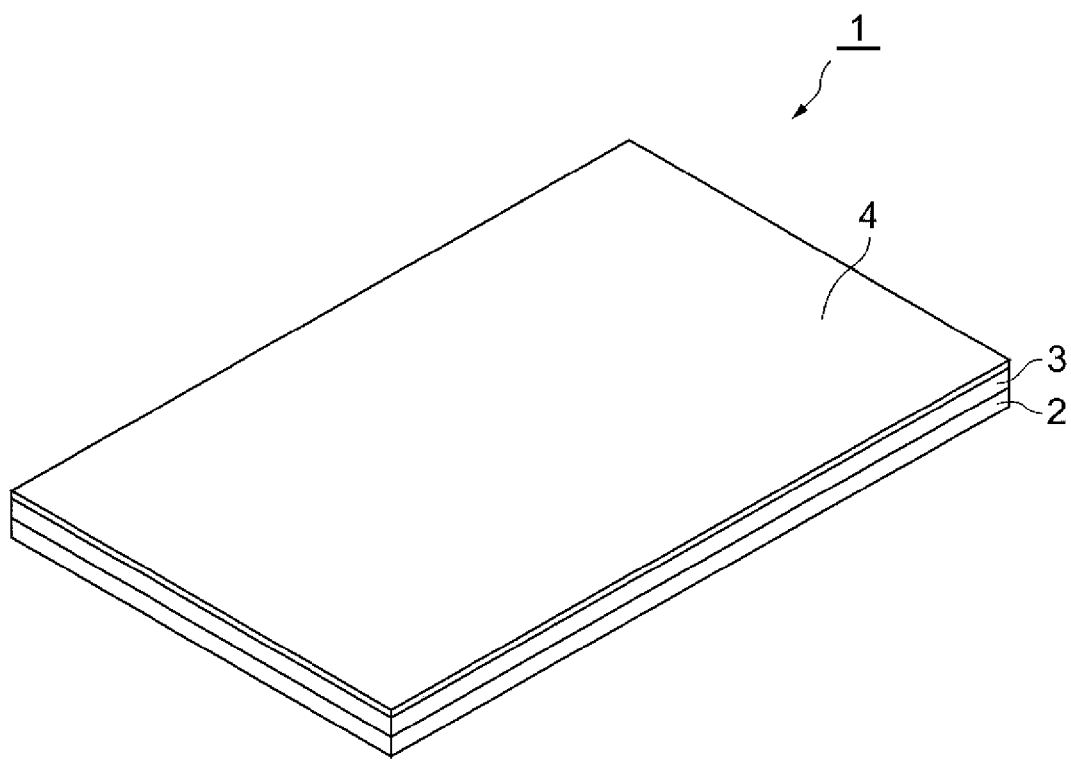
FIG. 1 is a perspective view of a preferred embodiment of the medicated patch of the invention.

FIG. 1 is a perspective view of a preferred embodiment of the medicated patch of the invention. In FIG. 1, the medicated patch 1 comprises a support 2, a pressure-sensitive adhesive layer 3 laminated on the support 2, and a release sheet 4 attached to the pressure-sensitive adhesive layer 3. The pressure-sensitive adhesive layer 3 contains a medicinal agent, an adhesive base material and a tackifire. The medicinal agent is varenicline or a pharmaceutically acceptable salt thereof, the adhesive base material is a rubbery adhesive base material and the tackifier is a rosin-based tackifier selected from the group consisting of rosins, rosin derivatives and hydrogenated products of the foregoing, or a non-rosin-based tackifier selected from the group consisting of aliphatic hydrocarbon resins and alicyclic hydrocarbon resins, and when a non-rosin-based tackifier is added as the tackifire, a solubilizer for the medicinal agent is further added, the solubilizer comprising an alcohol-based solubilizer having at least a solubility parameter of 20-35.

The pressure-sensitive adhesive layer 3 may consist of two or more laminated layers, and it may be laminated on both sides instead of only one side of the support 2. The release sheet 4 is peeled off before attachment for use.

The material of the support 2 is not particularly restricted so long as it can generally be used in a medicated patch, and it may be elastic or non-elastic. Specifically, there may be used a film or sheet formed of a synthetic resin such as polyethylene terephthalate, polyethylene, polypropylene, polybutadiene, ethylenevinyl acetate polymer, polyvinyl chloride, polyester, nylon or polyurethane, or a laminated body, porous membrane, foam, woven fabric or nonwoven fabric thereof, or a paper material.

The pressure-sensitive adhesive layer 3 contains an adhesive base material. The adhesive base material can serve as the base material of the pressure-sensitive adhesive layer 3, and a rubbery adhesive base material is used. The rubbery adhesive base material is preferably natural rubber, synthetic rubber, styrene-isoprene-styrene block copolymer (hereinafter abbreviated as "SIS"), isoprene rubber, polyisobutylene (hereinafter abbreviated as "PIB"), styrene-butadiene-styrene block copolymer (hereinafter abbreviated as "SBS"), styrene-butadiene rubber (hereinafter abbreviated as "SBR"), polybutene or the like. SIS is particularly preferred for use among these.

Such adhesive base materials may be used alone or in combinations of two or more. The content of the adhesive base material is preferably 10-95 wt %, more preferably 15-80 wt % and most preferably 15-50 wt % based on the total weight of the pressure-sensitive adhesive layer 3, in consideration of formation of the pressure-sensitive adhesive layer 3 and tissue permeability of the active ingredient.

The pressure-sensitive adhesive layer 3 contains a tackifire. The tackifier is a rosin-based tackifier selected from the group consisting of rosins, rosin derivatives and hydrogenated products of the foregoing, or a non-rosin-based tackifier selected from the group consisting of aliphatic hydrocarbon resins and alicyclic hydrocarbon resins. As rosin-based tackifiers there may be mentioned rosins, rosin esters, polymerized rosins, maleic acid-modified rosins and the like. As rosin esters there may be suitably used glycerin esters and pentaerythritol esters. The "hydrogenated forms" mentioned above are compounds wherein at least a portion of the unsaturated bonds of a rosin or rosin derivative have been reduced to saturated bonds. Examples of rosin-based tackifiers include ESTER GUM (Hydrogenated rosin ester) (trade name of Arakawa Chemical Industries, Ltd.), PINECRYSTAL (Hydrogenated rosin ester) (trade name of Arakawa Chemical Industries, Ltd.), HARIESTER (Gum rosin based esterified compounds) (trade name of Harima Chemicals, Inc.), PENTALYN (Phenolic modified rosin ester) (trade name of Eastman Chemical Company) and FORAL (Hydrogenated rosinate) (trade name of Eastman Chemical Company). Examples of non-rosin-based tackifiers include ARKON (Alicyclic hydrocarbon) (Arakawa Chemical Industries, Ltd.), QUINTONE (Hydrocarbon resin) (Zeon Corp.) and CLEARON (Hydrogenated terpene resin) (Yasuhara Chemical Co., Ltd.).

These tackifiers may be used as single types alone, or two or more thereof may be used in combination. The content of the tackifier is preferably 10-90 wt %, more preferably 15-70 wt % and most preferably 20-60 wt % based on the total weight of the pressure-sensitive adhesive layer 3, in consideration of sufficient pressure-sensitive adhesive force of the medicated patch 1 and low local irritation during peeling.

When the tackifier is a non-rosin-based tackifire, the pressure-sensitive adhesive layer 3 further contains a solubilizer for the medicinal agent. A solubilizer may also be added when the tackifier is a rosin-based tackifire. The solubilizer is an alcohol-based solubilizer with a solubility parameter of 20-35. The solubilizer is preferably a monohydric or polyhydric alcohol with a solubility parameter of 20-35, and more preferably a polyhydric alcohol with a solubility parameter of 20-35. As such solubilizers there may be mentioned propylene glycol and dipropylene glycol.

The pressure-sensitive adhesive layer 3 comprises varenicline or a pharmaceutically acceptable salt thereof, as a medicinal agent. The medicinal agent contains the free form of the medicinal agent salt obtained from the neutralization reaction, and the salt form remaining from incomplete neutralization.

Two or more of these medicinal agents may be used in combination if necessary, if this does not present an inconvenience by interaction. From the viewpoint of obtaining a sufficient drug effect as a medicated patch and in consideration of the physical properties and tissue absorption of the preparation, the content is preferably 0.5-50 wt % and most preferably 1-30 wt % based on the total weight of the pressure-sensitive adhesive layer 3.

The medicinal agent is preferably a medicinal agent produced from an acid addition salt. Examples of acid addition salt forms include hydrochlorides, acetic acid salts, sulfuric acid salts, maleic acid salts, oxalic acid salts, citric acid salts, hydroiodic acid salts, hydrobromic acid salts, mesylic acid salts, tartaric acid salts and succinic acid salts.

The pressure-sensitive adhesive layer 3 may comprise a metal salt containing a substance, or its constituent component, that can bond with the medicinal agent to form a medicinal agent salt. The metal salt is produced during the production process. Using an acid addition salt of the medicinal agent as the starting material and mixing it with a neutralizer causes neutralization reaction of the medicinal agent, so that the pressure-sensitive adhesive layer 3 will contain the free form of the medicinal agent which has higher tissue absorption, while also containing a metal salt produced by neutralization reaction of the medicinal agent.

The type of metal salt produced by the neutralization reaction (desalting reaction) is determined by the medicinal agent salt and the neutralizer used for neutralization. The metal salt produced when the acid addition salt of the basic medicinal agent is neutralized is preferably at least one selected from the group consisting of metal chlorides, metal bromides, metal iodides and organic acid metal salts, and among these it is preferably at least one type selected from sodium chloride, calcium chloride, aluminum chloride, stannous chloride, ferric chloride, magnesium chloride, potassium chloride, sodium citrate, sodium oxalate, sodium tartrate, sodium bromide and sodium succinate.

The neutralizer used for the neutralization reaction is not particularly restricted, but when a medicinal agent produced from an acid addition salt is used as the medicinal agent, a basic substance is suitable, while a strong base is suitable and an alkali metal hydroxide is especially preferred, for complete desalting of the medicinal agent acid addition salt. Specific examples of neutralizers include sodium hydroxide, potassium hydroxide and magnesium hydroxide, among which sodium hydroxide is especially preferred. The neutralizer is added to convert all or a portion of the medicinal agent to a free base (free form). In order to avoid decomposing the medicinal agent by excess neutralizer, the neutralizer is preferably added in a range of 0.5-4 equivalents with respect to the acid-base equivalents of the medicinal agent. The addition may be all at once or divided in several doses during the production process.

The medicated patch 1 of the invention may also contain a plasticizer, absorption accelerator, antioxidant, filler, crosslinking agent, preservative or ultraviolet absorber as necessary, in addition to the composition described above.

Examples of plasticizers include petroleum-based oils such as paraffin-based process oils, naphthene-based process oils and aromatic-based process oils; squalane and squalene; plant-based oils such as olive oil, camellia oil, castor oil, tall oil and peanut oil; dibasic acid esters such as dibutyl phthalate and dioctyl phthalate; liquid rubbers such as polybutene and liquid isoprene rubber; and diethylene glycol, polyethylene glycol, propylene glycol, dipropylene glycol and the like. Any of these may be used alone or in combinations of two or more.

Liquid paraffin and liquid polybutene are especially preferred for use for this embodiment.

The content of the plasticizer in the pressure-sensitive adhesive layer 3 is preferably 1-60 wt %, more preferably 2-50 wt % and most preferably 3-40 wt % based on the total weight of the pressure-sensitive adhesive layer 3, in consideration of maintaining sufficient pressure-sensitive adhesive force as a medicated patch 1.

As absorption accelerators there may be suitably used aliphatic alcohols such as isostearyl alcohol, fatty acids such as capric acid, fatty acid derivatives such as propyleneglycol monolaurate and isopropyl myristate, and propylene glycol, polyethylene glycol, diethanolamine laurate and the like. These absorption accelerators may be used alone or in combinations of two or more. The content of the absorption accelerator is preferably 1-30 wt %, more preferably 3-20 wt % and most preferably 5-15 wt % based on the total weight of the medicated patch 1, in consideration of obtaining sufficient permeability and low local irritation of the active ingredient with respect to tissue, for the obtained patch.

Examples of fillers include aluminum hydroxide, calcium carbonate, magnesium carbonate; silicic acid salts such as aluminum silicate and magnesium silicate; and silicic acid, barium sulfate, calcium sulfate, calcium zincate, zinc oxide, titanium oxide and the like.

As crosslinking agents there may be mentioned thermosetting resins such as amino resins, phenol resins, epoxy resins, alkyd resins, unsaturated polyesters, organic crosslinking agents such as isocyanate compounds and block isocyanate compounds, and inorganic crosslinking agents such as metals and metal compounds.

Examples of ultraviolet absorbers include p-aminobenzoic acid derivatives, anthranilic acid derivatives, salicylic acid derivatives, coumarin derivatives, amino acid-based compounds, imidazoline derivatives, pyrimidine derivatives, dioxane derivatives and the like.

These antioxidants, fillers, crosslinking agents, preservatives and ultraviolet absorbers may be added to a total of preferably no greater than 5 wt %, even more preferably no greater than 3 wt % and most preferably no greater than 1 wt %, based on the total weight of the pressure-sensitive adhesive layer 3.

The medicated patch preferably has an acid value of no greater than 28 and preferably no greater than 25. An acid value of no greater than 28 will tend to yield a medicated patch with high cutaneous permeability. The acid value is the value measured according to the Japanese Pharmacopeia. The measuring method may be the following method, for example.

First, a tetrahydrofuran/methanol/water mixture is added to the pressure-sensitive adhesive layer 1, and subjected to ultrasonic treatment to produce a uniform dispersion. A potassium hydroxide (hereunder abbreviated as KOH) aqueous solution is added dropwise to the solution and the pH is measured with a glass electrode/reference electrode. The neutralization point is the center point (point of inflection) where the pH changes abruptly, and when multiple points of inflection exist, the neutralization point is the point of inflection of highest pH. The dropwise addition amount calculated in the same manner with the solvent alone is subtracted as blank from the dropwise addition amount up to the neutralization point and considered the actual necessary amount of KOH, and the acid value is calculated from the following formula (I).

[Formula 1]

$$\text{Acid value} = [56.11 \text{ (g/mol)} \times \text{amount of KOH necessary for neutralization (mol)}]/\text{medicated patch weight 100 (mg)} \quad (1)$$

An example of a method for producing the medicated patch 1 of this embodiment will now be explained.

First, a mixture for formation of the pressure-sensitive adhesive layer 3 is prepared. A mixer is used to dissolve or disperse the adhesive base material, tackifire, medicinal agent acid addition salt, neutralizer and other components in the solvent for the adhesive base material, to obtain a mixture for formation of the pressure-sensitive adhesive layer 3.

The solvent for the adhesive base material may be toluene, hexane, ethyl acetate, cyclohexane, heptane, butyl acetate, ethanol, methanol, xylene, isopropanol or the like. These are appropriately selected according to the components to be dissolved or dispersed, and one may be used alone or a combination of two or more used together.

Next, the obtained mixture for formation of the pressure-sensitive adhesive layer 3 is spread directly onto a support 2 to form a pressure-sensitive adhesive layer 3, or it is spread onto a release-treated paper sheet or film to form the pressure-sensitive adhesive layer 3 and the support 2 situated thereover for contact transfer of the pressure-sensitive adhesive layer 3 onto the support 2. Next, a release sheet 4 for protection of the pressure-sensitive adhesive layer 3 is attached to the pressure-sensitive adhesive layer 3 to obtain a medicated patch 1.

When it is to be stored inside a package, the produced medicated patch 1 is preferably stored in the presence of a storage stabilizer. As storage stabilizers there may be used desiccants, deoxidizers and the like, and examples of common materials as desiccants include any substances with the capacity of physical or chemical adsorption, among which there may be mentioned zeolite, silica gel, alumina, molecular sieves and montmorillonite. Specifically, there may be mentioned Sorb-It (Absorbents & Desiccants Corporation of America) and PharmaKeep (Mitsubishi Gas Chemical Co., Inc.). The deoxidizer used for the invention is not particularly restricted so long as it can absorb, adsorb or remove oxygen. Various known deoxidizers can also be used. Examples include active iron oxide, hydrosulfite, butylhydroxytoluene and the like, in powdered, granular or tablet form. Commercial products include AGELESS (Mitsubishi Gas Chemical Co., Inc.) and VITALON (Toagosei Co., Ltd.).

EXAMPLES

The present invention will now be explained in detail by examples, with the understanding that the invention is not limited thereto, and various modifications may be made that are within the technical concept of the invention. The "%" values throughout the examples all signify weight percentages.

Example 1

An organic solvent was added to and mixed with varenicline tartrate, sodium hydroxide, liquid paraffin, SIS, an alicyclic hydrocarbon resin and propylene glycol (hereinafter abbreviated as PG), to obtain a uniform coating solution. This was spread onto a release-treated film, the solvent was removed by drying to form a pressure-sensitive adhesive layer, and then a support was placed thereover and the pressure-sensitive adhesive layer was contact transferred to obtain a percutaneous absorption-type medicated patch. Table 1 and Table 2 show the contents for each of Examples 1-4 and Comparative Examples 1-9.

Example 2

A percutaneous absorption-type medicated patch was obtained in the same manner as Example 1, except that dipropylene glycol was used instead of propylene glycol as the solubilizer.

Example 3

A percutaneous absorption-type medicated patch was obtained in the same manner as Example 1, except that a rosin ester was used instead of the alicyclic hydrocarbon resin as the tackifire, and no propylene glycol was added.

Example 4

A percutaneous absorption-type medicated patch was obtained in the same manner as Example 1, except that polyisobutylene was further added as a rubbery adhesive base material, and dipropylene glycol was used instead of propylene glycol.

Comparative Examples 1-8

Percutaneous absorption-type medicated patches were obtained for Comparative Examples 1-8 in the same manner as Example 1, except that octyldodecanol, isostearyl alcohol, isopropyl myristate, isopropyl palmitate, sorbitan monolaurate, sorbitan monooleate, triacetin and N-methyl-2-pyrrolidone were used instead of PG as the solubilizer.

Comparative Example 9

A percutaneous absorption-type medicated patch was obtained in the same manner as Example 1, except that no PG was added as a solubilizer.

(Evaluation of Medicinal Agent Crystal Deposition)

The outer appearances of the medicated patches of Examples 1-4 and Comparative Examples 1-9 were observed and the presence or absence of medicinal agent crystals was visually evaluated. Tables 1 and 2 show the type of solubilizers and tackifiers, and the presence of absence of crystals evaluated on the following scale:
A: absolutely no visible deposition of crystals
B: visible deposition of crystals,
immediately after and 1 month after preparation of the test patch.

(In Vitro Hairless Mouse Skin Permeation Test)

Figure 2:
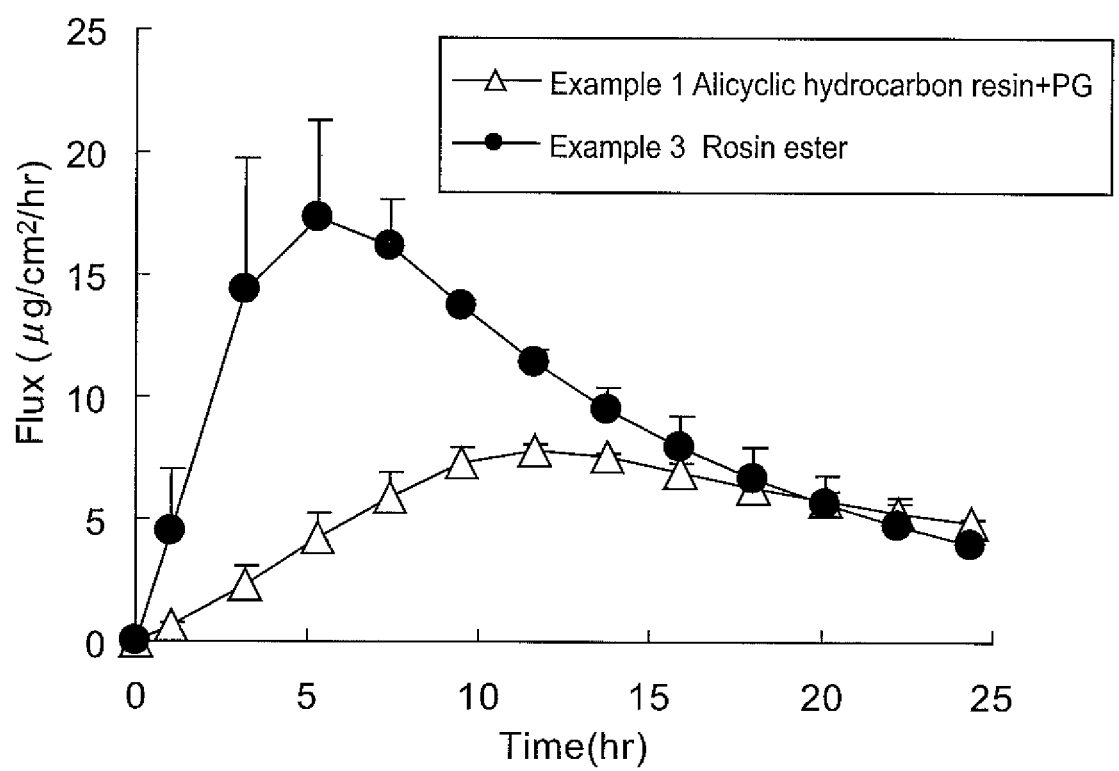
FIG. 2 is graph showing the effect on mouse cutaneous permeability by the tackifire.

Skin was peeled from the back of a hairless mouse and was fitted in a flow-through cell (5 cm$^2$) with the dermis side on the receptor layer side, and with exterior circulation of hot water set so that the skin surface temperature was 32° C. The patches of Examples 1-4 were each attached to the stratum corneum side, and phosphate-buffered saline at pH 7.4 was used on the receptor layer and sampled up to 24 hours every 120 minutes, at a rate of 5 mL/hr. The flow rate of the obtained receptor solution was measured precisely every hour, and the medicinal agent concentration was measured by high performance liquid chromatography. The permeation rate per hour was calculated from the measured values for the flow rate and medicinal agent concentration, and the maximum skin permeation rate (maximum flux) was determined for each example. The results are shown in Table 1. FIG. 2 shows the permeation profiles for Example 1 and Example 3.

TABLE 1

|  |  | Example 1 | Example 2 | Example 3 | Example 4 | Comp. Ex. 1 | Comp. Ex. 2 | Comp. Ex. 3 |
|---|---|---|---|---|---|---|---|---|
| Varenicline tartrate | | 5.0 | 5.0 | 5.0 | 5.0 | 5.0 | 5.0 | 5.0 |
| Sodium hydroxide | | 1.1 | 1.1 | 1.1 | 1.1 | 1.1 | 1.1 | 1.1 |
| Liquid paraffin | | 18.9 | 18.9 | 23.9 | 21.8 | 18.9 | 18.9 | 18.9 |
| SIS | | 20.0 | 20.0 | 20.0 | 18.8 | 20.0 | 20.0 | 20.0 |
| Polyisobutylene | | — | — | — | 8.1 | — | — | — |
| Adhesiveness-imparting agent | Alicyclic hydrocarbon resin | 50.0 | 50.0 | — | 40.2 | 50.0 | 50.0 | 50.0 |
|  | Rosin ester | — | — | 50.0 | — | — | — | — |
| Solubilizer | PG | 5.0 | — | — | — | — | — | — |
|  | Dipropylene glycol | — | 5.0 | — | 5.0 | — | — | — |
|  | Octyldodecanol | — | — | — | — | 5.0 | — | — |
|  | Isostearyl alcohol | — | — | — | — | — | 5.0 | — |
|  | Isopropyl myristate | — | — | — | — | — | — | 5.0 |
| Evaluation of crystal deposition | | A | A | A | A | B | B | B |
| Maximum FLUX (μg/cm$^2$/hr) | | 7.9 | 10.0 | 17.3 | 8.2 | — | — | — |

(Addition units: parts by weight)

TABLE 2

|  |  | Comp. Ex. 4 | Comp. Ex. 5 | Comp. Ex. 6 | Comp. Ex. 7 | Comp. Ex. 8 | Comp. Ex. 9 |
|---|---|---|---|---|---|---|---|
| Varenicline tartrate | | 5.0 | 5.0 | 5.0 | 5.0 | 5.0 | 5.0 |
| Sodium hydroxide | | 1.1 | 1.1 | 1.1 | 1.1 | 1.1 | 1.1 |
| Liquid paraffin | | 18.9 | 18.9 | 18.9 | 18.9 | 18.9 | 23.9 |
| SIS | | 20.0 | 20.0 | 20.0 | 20.0 | 20.0 | 20.0 |
| Adhesiveness-imparting agent | Alicyclic hydrocarbon resin | 50.0 | 50.0 | 50.0 | 50.0 | 50.0 | 50.0 |
|  | Rosin ester | — | — | — | — | — | — |
| Solubilizer | Isopropyl palmitate | 5.0 | — | — | — | — | — |
|  | Sorbitan monolaurate | — | 5.0 | — | — | — | — |
|  | Sorbitan monooleate | — | — | 5.0 | — | — | — |
|  | Triacetin | — | — | — | 5.0 | — | — |
|  | N-methyl-2-pyrrolidone | — | — | — | — | 5.0 | — |
| Evaluation of crystal deposition | | B | B | B | B | B | B |
| Maximum FLUX (μg/cm$^2$/hr) | | — | — | — | — | — | — |

(Addition units: parts by weight)

Table 3 shows the solubility parameters for the solubilizers used in Examples 1-4 and Comparative Examples 1-8. Calculation of the solubility parameters was performed using a Molecular Modeling Pro (ChemSW, Inc.) (Hansen's 3-D solubility parameters).

TABLE 3

| Solubilizer | Solubility parameter (δ/spr (MPa)) |
|---|---|
| Propylene glycol | 30.2 |
| Dipropylene glycol | 26.3 |
| Octyldodecanol | 18.5 |
| Isostearyl alcohol | 17.0 |
| Isopropyl myristate | 16.0 |
| Isopropyl palmitate | 15.7 |
| Sorbitan monolaurate | 21.8 |
| Sorbitan monooleate | 21.8 |
| Triacetin | 27.2 |
| N-Methyl-2-pyrrolidone | 23.0 |

INDUSTRIAL APPLICABILITY

According to the invention there is provided a medicated patch comprising varenicline or a pharmaceutically acceptable salt thereof as the medicinal agent, and having both excellent medicinal agent solubility and tissue permeability.

The invention claimed is:

1. A medicated patch composition comprising a medicinal agent, an adhesive base material, a tackifier and a solubilizer for the medicinal agent,
   wherein the medicinal agent is varenicline or a pharmaceutically acceptable salt thereof,
   the adhesive base material is a rubbery adhesive base material,
   the tackifier is a non-rosin-based tackifier selected from the group consisting of aliphatic hydrocarbon resins and alicyclic hydrocarbon resins, and
   the solubilizer is an alcohol-based solubilizer having a solubility parameter of 20-35.

2. The medicated patch composition according to claim 1, wherein the content of the adhesive base material is 15-50 wt %.

3. The medicated patch composition according to claim 1, wherein the solubilizer is a polyhydric alcohol with a solubility parameter of 25-35.

4. The medicated patch composition according to claim 1, wherein the solubilizer is propylene glycol or dipropylene glycol.

5. A medicated patch comprising a support and a pressure-sensitive adhesive layer containing a medicated patch composition according to claim 1 provided on the support.

6. A method for preventing crystal deposition of a medicinal agent in a medicated patch, comprising:
   providing a medicated patch composition comprising a medicinal agent, an adhesive base material, a tackifier and a solubilizer for the medicinal agent,
   wherein the medicinal agent is varenicline or a pharmaceutically acceptable salt thereof,
   the adhesive base material is a rubbery adhesive base material,
   the tackifier is a non-rosin-based tackifier selected from the group consisting of aliphatic hydrocarbon resins and alicyclic hydrocarbon resins, and
   the solubilizer is an alcohol-based solubilizer having a solubility parameter of 20-35.

* * * * *